US006186792B1

United States Patent
Discko

(10) Patent No.: US 6,186,792 B1
(45) Date of Patent: Feb. 13, 2001

(54) METHOD OF COATING WITH A DISPOSABLE DENTAL APPLICATOR

(75) Inventor: John J. Discko, Trumbull, CT (US)

(73) Assignee: Centrix, Inc., Shelton, CT (US)

( * ) Notice: Under 35 U.S.C. 154(b), the term of this patent shall be extended for 0 days.

(21) Appl. No.: 09/517,549

(22) Filed: Mar. 2, 2000

Related U.S. Application Data

(62) Division of application No. 08/934,983, filed on Sep. 22, 1997, now Pat. No. 6,049,934.

(51) Int. Cl.[7] .................................................. A61C 5/08
(52) U.S. Cl. .............................................. 433/220; 433/81
(58) Field of Search .................... 433/220, 224, 433/226, 217.1, 102, 81

(56) References Cited

U.S. PATENT DOCUMENTS

| | | | |
|---|---|---|---|
| D. 329,142 | 9/1992 | Discko, Jr. et al. | D4/104 |
| 890,143 | 6/1908 | Kuzzer | 15/106 |
| 2,229,664 | 1/1941 | Meeske | 15/106 |
| 2,386,085 | 10/1945 | Babel | 15/167.1 |
| 2,803,029 | 8/1957 | Brady | 15/106 |
| 3,720,975 | 3/1973 | Nelson | 15/206 |
| 3,818,911 | 6/1974 | Fournier | 15/244.2 |
| 4,030,199 | 6/1977 | Russell | 15/106 |
| 5,009,593 * | 4/1991 | Vogelstein | 433/221 |
| 5,150,495 | 9/1992 | Discko, Jr. et al. | 15/167.1 |
| 5,350,298 * | 9/1994 | Delaire | 433/81 |
| 5,414,890 | 5/1995 | Morendo | 15/167.1 |
| 5,459,898 | 10/1995 | Bacolot | 15/106 |
| 5,604,952 * | 2/1997 | Zeleznick | 15/167.1 |
| 5,632,620 * | 5/1997 | Musikant et al. | 433/102 |
| 5,647,746 * | 7/1997 | Chipman | 433/226 |

FOREIGN PATENT DOCUMENTS

| | | |
|---|---|---|
| 39 37 030 C2 | 5/1990 | (DE) . |
| 7787 | 6/1886 | (GB) . |
| 561300 | 5/1944 | (GB) . |

* cited by examiner

Primary Examiner—John J. Wilson
Assistant Examiner—Melba Bumgarner
(74) Attorney, Agent, or Firm—Fattibene & Fattibene; Paul A. Fattibene; Arthur T. Fattibene

(57) ABSTRACT

A tubular applicator handle having an applicator integrally formed on either end. The applicable integrally formed on either end may be a brush, foam pad, fuzzy ball or other similar or equivalent applicator, for applying a liquid, paste or powder. The applicator may be use in a method of coating a post hole with a dental material. The present invention has particular adaptability in the dental field for applying dental materials.

1 Claim, 6 Drawing Sheets

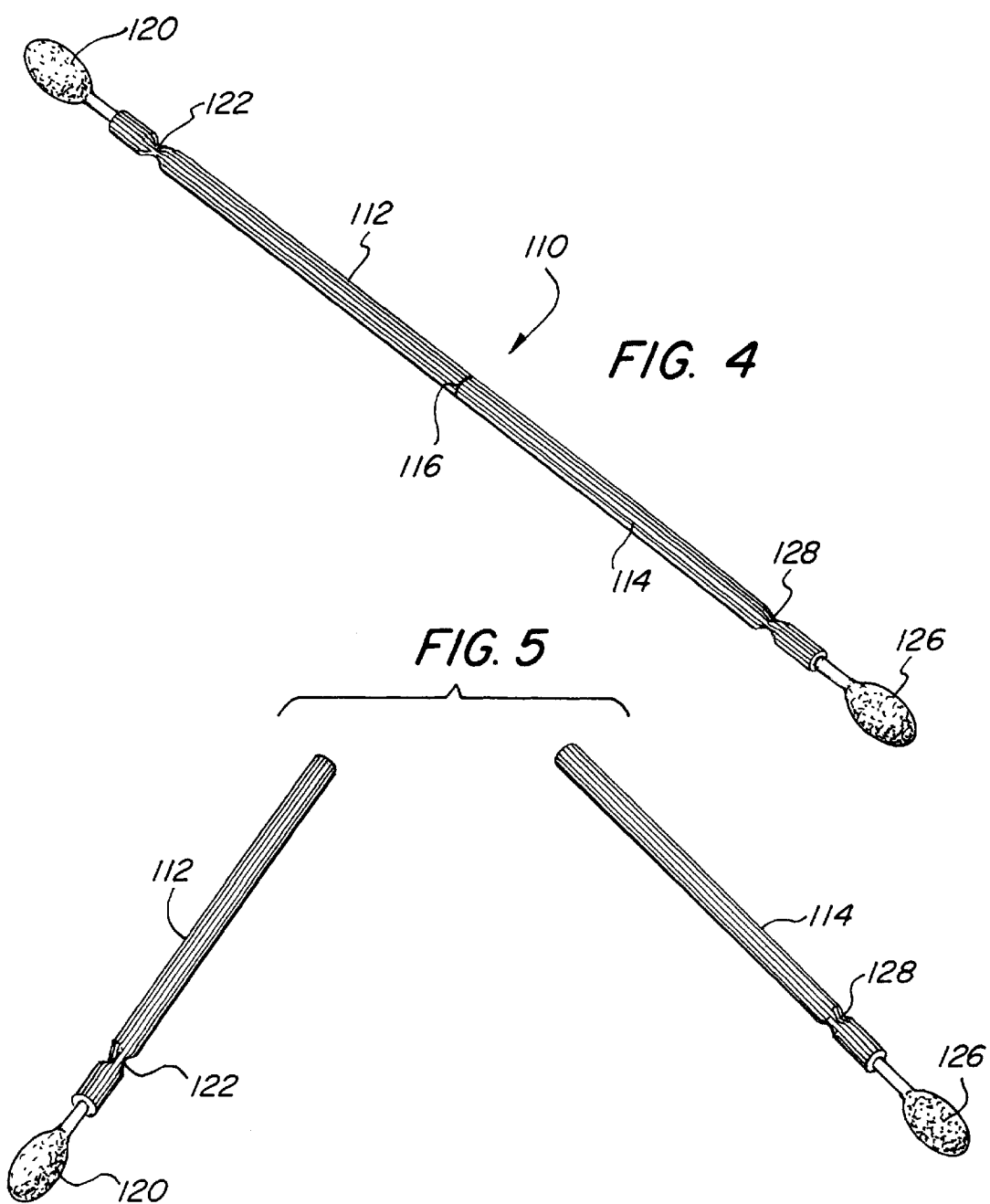

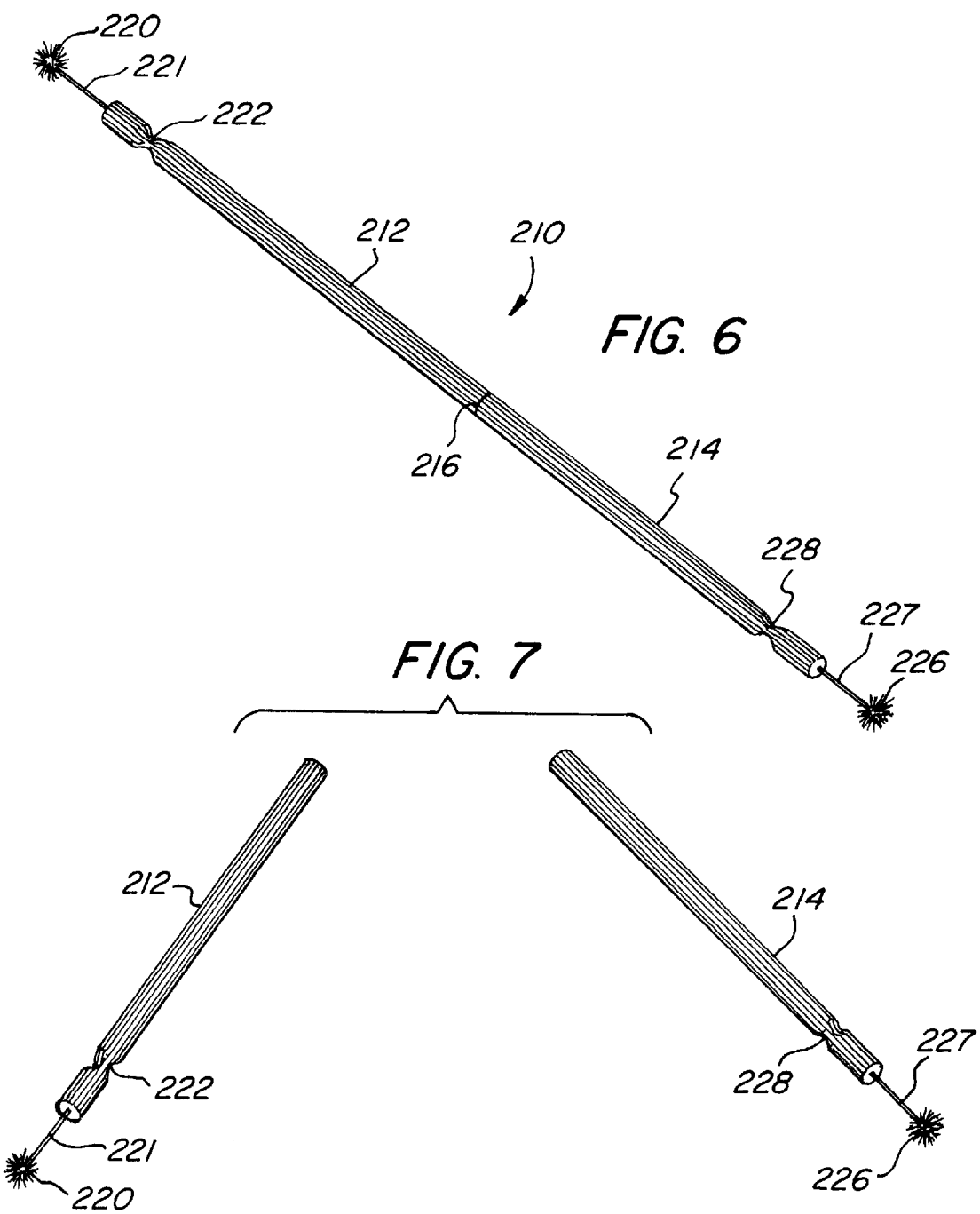

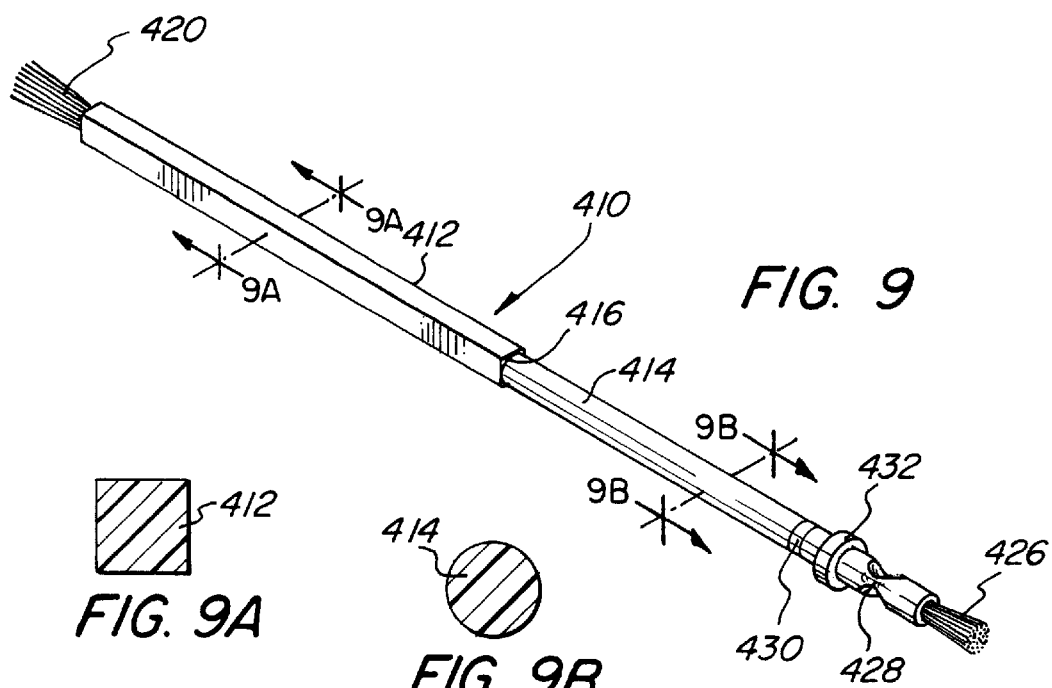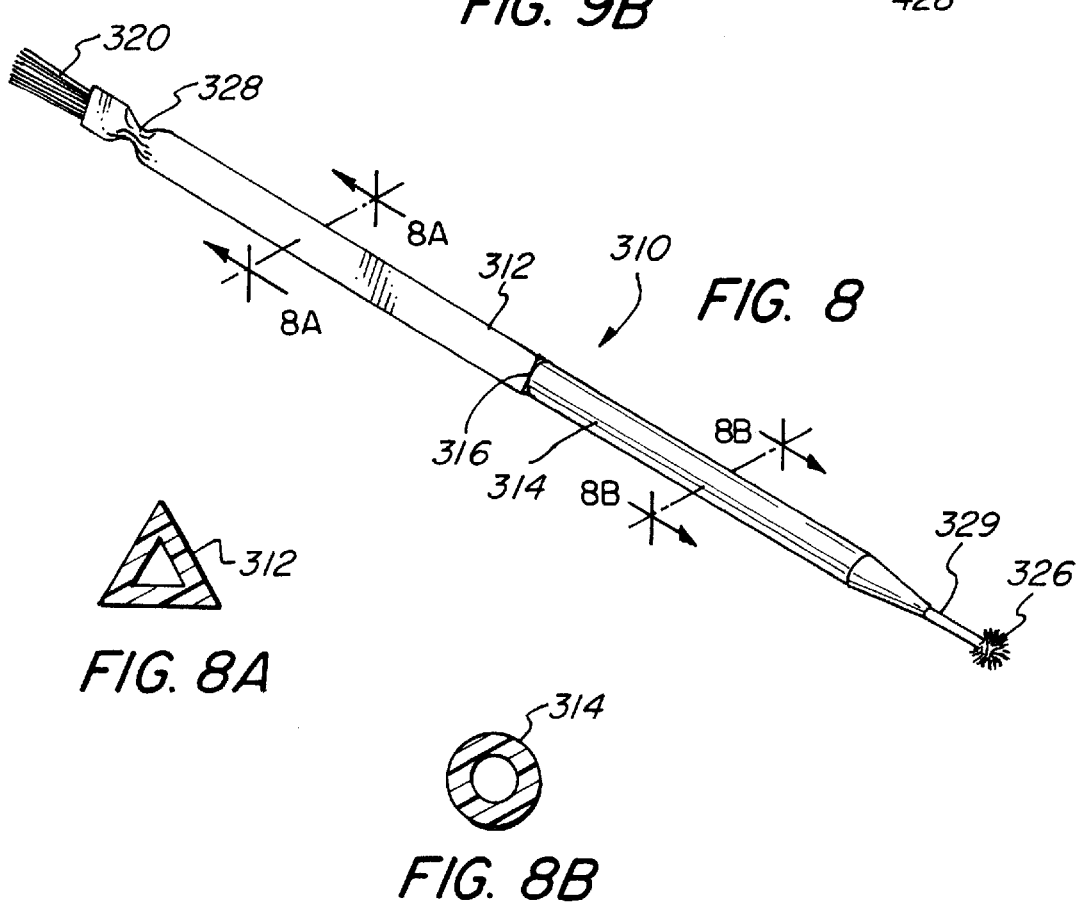

METHOD OF COATING WITH A DISPOSABLE DENTAL APPLICATOR

RELATED APPLICATION

This application is a divisional of U.S. patent application Ser. No. 08/934,983 filed Sep. 22, 1997 now U.S. Pat. No. 6,049,934, which is herein incorporated by reference.

FIELD OF THE INVENTION

The present invention relates to a disposable applicator for applying different dental materials, and in particular to a disposable dental applicator used to apply dental materials to a post hole in a tooth.

BACKGROUND OF THE INVENTION

Applicators such as brushes, foam pads, cotton fiber or other applicators, are used to apply a variety of materials in many applications. Such applicators are of particular use in dentistry for applying various dental materials. Due to the risk of cross-contamination, it is desirable to use an applicator only once, after which the applicator is discarded. As a result, it is necessary to produce an applicator that is efficient and easy to handle at a low cost. A disposable dental brush is disclosed in U.S. Pat. No. 5,150,495 issuing to Discko et al on Sep. 29, 1992, entitled "Disposable Dental Brush", which is herein incorporated by reference. Therein disclosed is a disposable dental brush for applying various dental materials that includes an elongated handle having a tuft of bristles constructed so as to allow the portion thereof adjacent to the brush end to be readily bent so as to angularly dispose the brush relative to the longitudinal axis of the handle. Also disclosed therein is a brush end comprising a relatively short tubular holder or sleeve which has a bore extending therethrough such that the brush end is detachably connected to the free end of a handle by a frictional retention in the tubular brush holder. The dentist may use this construction as a single ended dental brush or alternatively, as a double ended brush, which allows the dentist to use the same brush for working with and applying different materials to a patient's teeth. Upon completion of a given procedure, the brush end or ends are rendered readily disposable. While this brush configuration has been adequate, it is not without some inconveniences. For example, the brush end that attaches to the handle is relatively small and difficult to manipulate and place on the handle. This is especially difficult when a dentist is wearing gloves. Additionally, the short brush portion results in the attached handle sometimes being inserted into the patient's mouth. This compromises the use of the attached handle portion in that it must be disinfected. Therefore, there is a need for an improved disposable applicator that is easy to handle, is inexpensive to manufacture, and produces less waste.

SUMMARY OF THE INVENTION

The present invention is a double ended applicator. An elongated handle has an applicator permanently attached to either end. The applicator may be a tuft of bristles, a foam pad, a fuzzy plastic brush, or any equivalent applicator made of different materials. The two applicator ends of the elongated handle may be color coded or shaped to distinguish the applicator ends. Additionally, each end of the applicator handle may be formed so as to bend such that the applicator end may be displaced at an angle relative to the longitudinal axis of the applicator handle. Additionally, a scribe, score line or frangible portion may be placed intermediate either end of the applicator ends so that the applicator handle may be broken or separated into two separate and independent single ended applicators.

Several embodiments are particularly adapted to coating a post hole in a tooth.

Accordingly, it is an object of the present invention to provide an economical, disposable applicator that is more efficient for coating a post hole in a tooth.

It is a further object of the present invention to provide an applicator that is easily manufactured.

It is an advantage of the present invention that it is easy to use and handle.

It is a further advantage of the present invention that it results in less waste.

It is yet a further advantage of the present invention that it results in time and motion savings for the user in that two different materials can quickly be used and applied by rotating the handle.

It is a feature of the present invention that an applicator is permanently attached to either end.

It is another feature of the present invention that one end is marked or shaped to identify it.

It is yet another feature of the present invention that a scribe, score line, or frangible portion may be formed intermediate either end.

It is a further feature of the present invention that the ends may be color coded.

These and other objects, advantages, and features will become readily apparent in view of the following more detailed description.

BRIEF DESCRIPTION OF THE DRAWINGS

FIG. 4 is a side elevational view of another embodiment of the present invention.

FIG. 5 is a side elevational view of another embodiment of the present invention after being separated.

FIG. 6 is a side elevational view of another embodiment of the present invention.

FIG. 7 is a side elevational view of another embodiment of the present invention after being separated.

FIG. 8 is a side elevational view of another embodiment of the present invention.

FIG. 8A is a cross section taken along line 8A—8A in FIG. 8.

FIG. 8B is a cross section taken along line 8B—8B in FIG. 8.

FIG. 9 is a side elevational view of another embodiment of the present invention.

FIG. 9A is a cross section taken along line 9A-9A in FIG. 9.

FIG. 9B is a cross section taken along line 9B—9B in FIG. 9.

DETAILED DESCRIPTION OF THE PREFERRED EMBODIMENT

Figure 1:
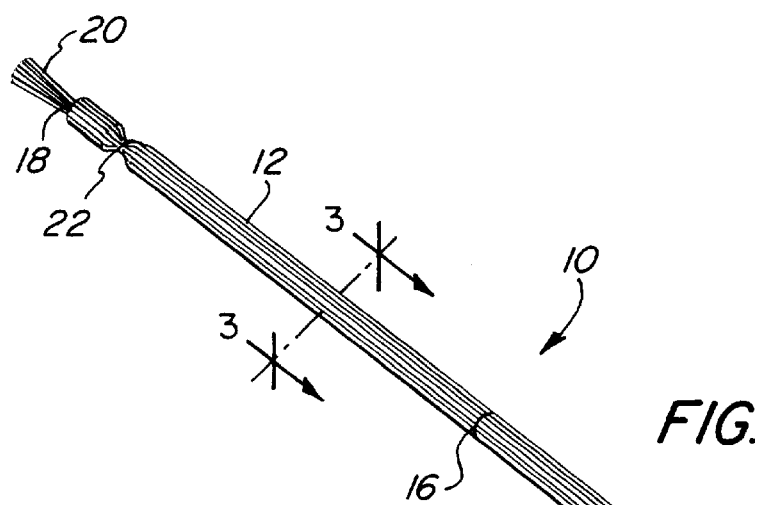
FIG. 1 is a side elevational view of the present invention.

FIG. 1 illustrates a single use or disposable applicator brush 10. The applicator brush 10 is made from an extruded tubular plastic material. The disposable applicator brush 10 has a first handle portion 12 and a second handle portion 14. Separating the first handle portion 12 and the second handle portion 14 is a score or scribe line 16. The score or scribe line 16 is a cut or indentation extending radially into the disposable applicator brush 10 around its circumference so as to form a readily separable or frangible portion or means for separating the first and second handle portions 12 and 14. The score or scribe line 16 is preferably located at the longitudinal center of the applicator brush 10. First handle portion 12 has a first bore 18 therein. Within first bore 18 is permanently attached an applicator, for example a first tuft of bristles 20. Near or adjacent the first tuft of bristles 20, is a bendable portion 22 which may be a crimp or hinge. The first bendable portion 22 permits the applicator end to be positioned at an angle with respect to the longitudinal axis of the first handle portion 12. Similarly, second handle portion 14 has a second bore 24 therein. Placed within the second bore is a second applicator, for example a second tuft of bristles 26. Near or adjacent the second tuft of bristles 26 is a second bendable portion 28, for example a crimp or a hinge. The first tuft of bristles 20 may have a color that is distinct from the second tuft of bristles 26. For example, the first tuft of bristles 20 may be white, and the second tuft of bristles 26 may be black. However, any distinct color may be used. This is so that a user, such as a dentist, can easily distinguish either end. This is advantageous when different materials are being used for each applicator end. Additionally, the first and second handle portions 12 and 14 may be color coded to distinguish them from each other or form other handle poritons.

Figure 2:
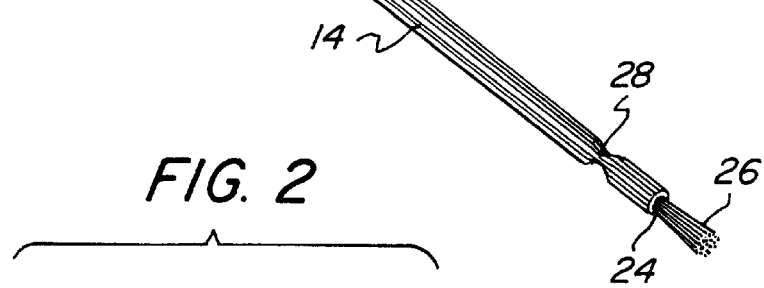
FIG. 2 is a side elevational view of the present invention after being separated.

FIG. 2 illustrates the applicator brush as illustrated in FIG. 1 after being separated along the score or scribe line 16 into two individual applicator brushes. The score or scribe line 16 illustrated in FIG. 1 permits the applicator brush 10 to be easily broken or separated along the score or scribe line 16, forming the two independent and separate applicator brushes illustrated in FIG. 2. Accordingly, a first applicator brush has a first handle portion 12, a first tuft of bristles 20, and a bendable portion 22. This first applicator brush may be used independently of the second applicator brush. The dentist or user can then choose to use either a single double ended applicator brush, or two independent single ended applicator brushes. This is a great convenience to the user or dentist and greatly reduces waste. The second applicator brush is formed from the second handle portion 14 having a second tuft of bristles 26 and a second bendable portion 28. Accordingly, from a single applicator brush having applicator brushes integrally formed at either end, two independent and separate applicator brushes may quickly and easily be formed by a user, such as a dentist, greatly reducing cost and increasing convenience to the user. The user can elect to use a single, double ended integrally or permanently attached applicator brushes attached to a single handle, or to separate the double ended applicator brush into two independent and individual applicator brushes which can be used at different times. As a result, waste is reduced by approximately fifty percent over more conventional single ended applicator brushes. Preferably, the applicator brush 10 has a combined longitudinal length of over four inches or 10.16 centimeters. This is so that each handle portion 12 and 14 has a length that is convenient to hold.

Figure 3:
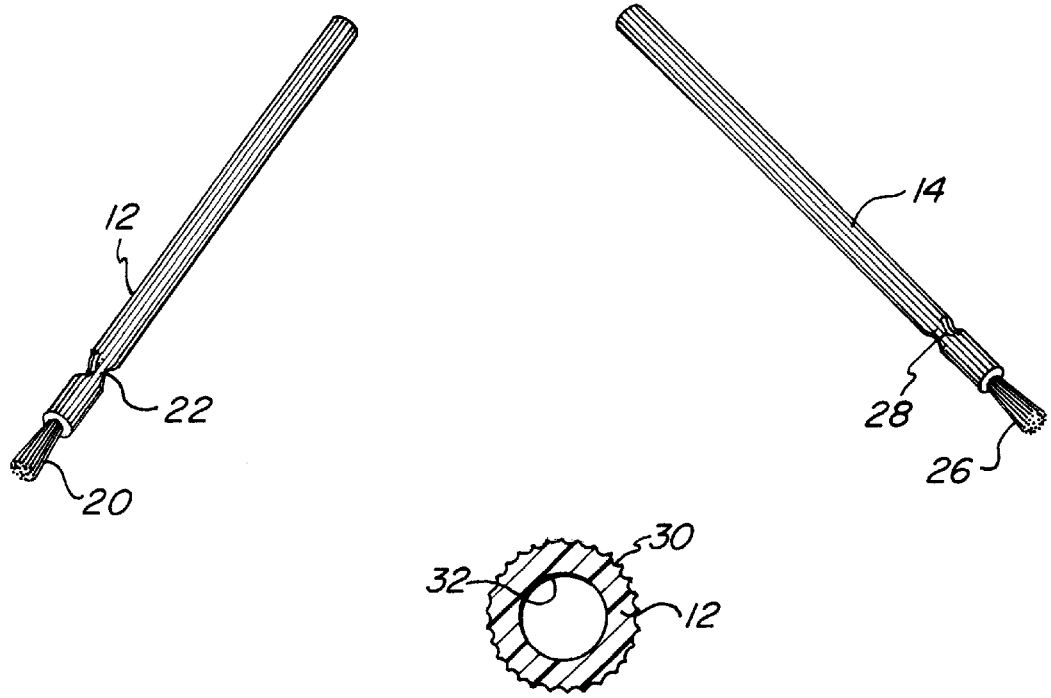
FIG. 3 is a cross section taken along line 3—3 in FIG. 1.

FIG. 3 is a cross section taken along line 3—3 in FIG. 1. The first handle portion 12 has an inner bore 32. On the exterior surface of the first handle portion 12 are ridges or ribs 30. The ridges or ribs 30 facilitate the holding and manipulation or rotating of the applicator brush by a user.

FIGS. 4 and 5 illustrate another embodiment of the present invention where the applicator portion is a foam pad. The disposable applicator device 110 has a first handle portion 112 and a second handle portion 114. A scribe or score line 116 is placed between the first handle portion 112 and the second handle portion 114. On one end of the first handle portion 112 is a permanently attached foam pad 120. The foam pad 120 may also be made of cotton fiber. Adjacent the foam pad 120 is a first bendable portion 122. The first foam pad 120 is permanently attached or integrally formed within the first handle 112. On one end of the second handle portion 114 is a second foam pad 126. The foam pad 126 may also be made of cotton fiber. The second foam pad 126 is permanently attached to the second handle portion 114. Adjacent or near the foam pad 126 is a bendable portion 128. The bendable portion 128 may be formed by a hinge or a crimp. FIG. 5 illustrates the separation along the score or scribe line 116 of the first handle portion 112 and the second handle portion 114. Accordingly, two separate independent applicators are formed. This greatly reduces waste.

FIGS. 6 and 7 illustrate another embodiment of the present invention having a fuzzy type applicator on either end. The applicator device 210 has a first handle portion 212 and a second handle portion 214. The first and second handle portions 212 and 214 are separated by a scribe or score line 216. On one end of the first handle portion 212 is a first rod or stick 221 having a fuzzy ball or micro brush 220 on one end. Adjacent the first rod 221 is a bendable portion 222 which may be a hinge or a crimp. The second handle portion 214 has a second rod or stick 227 with a fuzzy ball or micro brush 226 attached thereto. Adjacent the rod or stick 227 is a second bendable portion 228 which may be a crimp or a hinge. FIG. 7 illustrates the applicator device 210 after being separated or broken along the scribe or score line 216 forming two independent and separate applicators.

FIGS. 8, 8A and 8B illustrate another embodiment of the present invention. In this embodiment handle portions may be of different geometric shapes. In, FIG. 8 applicator device 310 is illustrated. Applicator device 310 has a first handle portion 312 and a second handle portion 314. The first handle portion 312 has a first geometric shaped cross section, and the second handle portion 314 has a second geometric shaped cross section. For example, the first geometric shaped cross section is a triangle and the second geometric cross section is a circle. Between first handle portion 312 and the second handle portion 314 is a frangible portion, scribe, or score line 316 which facilitates separating the first and second handle portions 312 and 314. On the distal end of the first handle portion 312 is a tuft of bristles 320. Adjacent the tuft of bristles 320 is a hinge or crimp 328.

On the distal end of the second handle portion 314 is a fuzzy or flock ball 326. Adjacent the fuzzy or flock ball 326 is a reduced diameter portion 329. The reduced diameter portion improves visibility and facilitates bending. FIG. 8A more clearly illustrates the triangular cross section taken along line 8A—8A in FIG. 8 of the first handle portion 312. FIG. 8B more clearly illustrates the circular cross section taken along line 8B—8B in FIG. 8 of the second handle portion 314. While FIGS. 8, 8A and 8B illustrate geometric cross sections of a triangle and a circle, it should be appreciated that any geometric shaped cross section could be used as long as the cross section of the first handle portion 312 is readily distinguishable from the cross section of the second handle portion 314. Additionally, while a tuft of bristles 320 and a fuzzy or flock ball 326 has been illustrated is should be appreciated that any type of applicator material could be used.

FIGS. 9, 9A and 9B illustrate another embodiment of the present invention. In this embodiment other identifying means are used. Additionally, a handle portion is illustrated as solid. In, FIG. 9 applicator device 410 is illustrated. Applicator device 410 has a first handle portion 412 and a second handle portion 414. The first handle portion 412 has a first geometric shaped cross section, and the second handle portion 414 has a second geometric shaped cross section. For example, the first geometric shaped cross section is a square and the second geometric cross section is a circle. Between first handle portion 412 and the second handle portion 414 is a frangible portion, scribe, or score line 416 which facilitates separating the first and second handle portions 412 and 414. On the distal end of the first handle portion 412 is a first tuft of bristles 420. On the distal end of the second handle portion 414 is a second tuft of bristles 426. Adjacent the second tuft of bristles 426 is a hinge or crimp 428. Adjacent the hinge or crimp 428 is a three dimensional marking 432. Adjacent the three dimensional marking is a colored stripe, ring, or band 430. Accordingly, the three dimensional marking 432 and the colored strip or band 430 illustrate different techniques for identifying one applicator. The three dimensional marking 432 is illustrated as a raised section around the circumference of the second handle portion 414. However, any raised three dimensional marking may be used. The three dimensional markings may be molded as an integral part of the applicator device 410. The colored strip or band 430 may be molded into the applicator device 410 or applied later with ink, dye, or paint. It should be appreciated that either band 430 or three dimensional marking 432 could be used at one end. Clearly, both would not be needed, but have only been shown together to illustrate that any identifying marks may be used. FIG. 9A more clearly illustrates the square cross section taken along line 9A—9A in FIG. 9 of the first handle portion 412. FIG. 9B more clearly illustrates the circular cross section taken along line 9B—9B in FIG. 9 of the second handle portion 414. FIG. 9B also illustrates the solid structure of the second handle portion 414. While only the first and second handle portion 412 and 414 are illustrated as solid, it should be appreciated that any of the handle portions illustrated in the other figures could be made solid.

Figure 10:
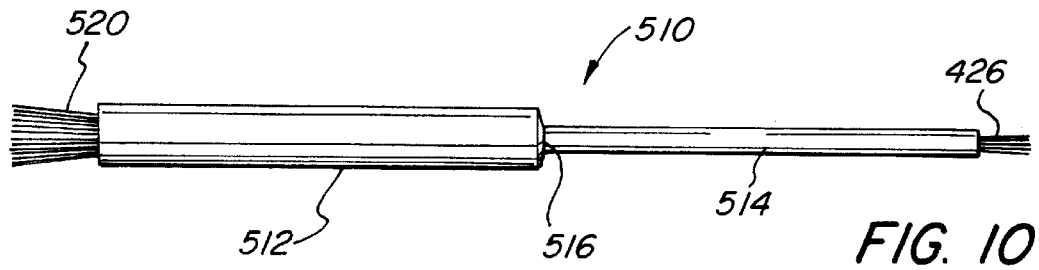
FIG. 10 is a side elevational view of another embodiment of the present invention.

FIG. 10 illustrates another embodiment of the present invention. In this embodiment the applicator device 510 has different size handle portions. The first handle portion 512 has a larger diameter or lateral dimension than the second handle portion 514. The larger first handle portion 512 has a relatively large tuft of bristles 520 therein. The smaller second handle portion 514 has a smaller tuft of bristles 426 therein. A scribe or score line is placed between the adjacent first and second handle portions 512 and 514. The separation of the two handle portions 512 and 514 is also facilitated by the different diameters or lateral dimensions of the first and second handle portions 512 and 514. This embodiment also has the advantage of providing two different brush sizes that are easily identifiable.

Figure 11:
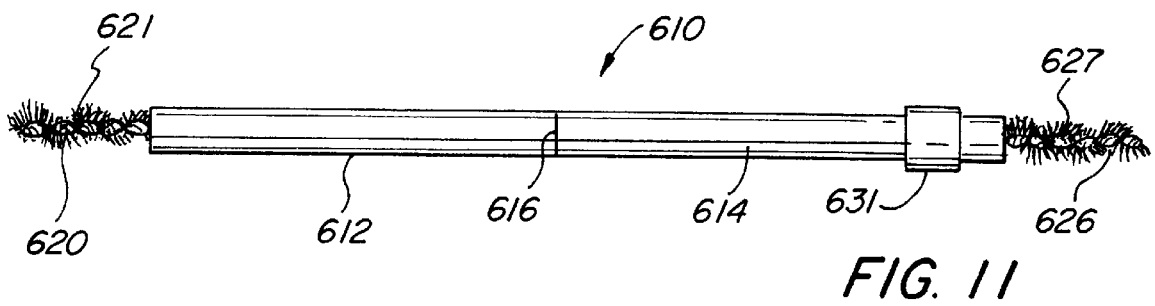
FIG. 11 is a side elevational view of another embodiment of the present invention.

FIG. 11 illustrates an applicator device 610 that is especially adapted for use in procedures involving dental post. The applicator device 610 may be a cylindrical tube and has a first handle portion 612 and a second handle portion 614. The first and second handle portions are separated by a scribe or score line 616. On the distal end of the first handle portion 612 is a first twisted wire 621 having an applicator material such as flock or brush bristles 620 twisted therein. The twisted wire is helically shaped having spirals. Accordingly, the flock or brush bristles 620 form a helix or spiral. The twisted wire 621 is inserted and held within the distal end of the first handle portion 612. On the distal end of the second handle portion 614 is a second twisted wire 627 having flock or brush bristles 626 twisted therein. The second twisted wire 627 is helically shaped similar to the first twisted wire 621. A flat crimp 631 may be used to hold the second twisted wire 627 within the second handle portion 614. The flat crimp 631 also functions to distinguish one end of the applicator device 610 from the other end. The embodiment of the present invention illustrated in FIG. 11 is particularly suited for applying dental etchants, primers, bonding agents and other agents to the walls of a post hole. Post holes are required in many dental procedures that need a post to be inserted into a tooth. A post hole is usually relatively narrow and deep resulting in difficulty in inserting a conventional bristle of brushes. The conventional bristle of brushes tends to fan out or splay when attempted to be inserted into a post hole. Additionally, the conventional bristle of brushes can not easily apply material to the side walls of the narrow post hole. The embodiment of the present invention illustrated in FIG. 11 greatly facilitates the application of materials or agents to the bottom and sides of post holes. The flock or brush bristles 620 and 626 extending the length of the twisted wires 621 and 627 makes possible more complete application of materials to the sides of post holes. Additionally, the helix formed by the twisted wires 621, 627 and flock or brush bristles 620, 626 results in material being pumped up and down the length of the twisted wires 621, 627 and flock or brush bristles 620, 626 when the applicator device 610 is rotated along the longitudinal axis. This assures that material reaches and coats or is applied to the bottom and sides of the post hole.

Figure 11A:
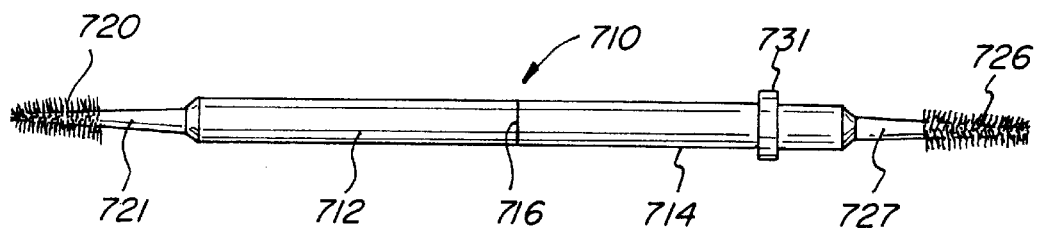
FIG. 11A is a side elevational view of another embodiment of the present invention.

FIG. 11A is another embodiment of the present invention similar to FIG. 11A. In FIG. 11A an applicator 710 is illustrated that is particular well suited for applying dental materials to the inner surfaces of a post hole. The applicator device 710 has a first handle portion 712 and a second handle portion 714. The first and second handle portions are separated by a scribe or score line 716. A first reduced diameter portion 721 extends from first handle portion 712. A second reduced diameter portion 727 extends from second handle portion 714. Adjacent the distal end of the first reduced diameter portion 721 is a first brush or flock 720. Adjacent the distal end of the second reduced diameter portion 727 is a second brush or flock 726. The first and second reduced diameter portions 721 and 727 are conical in shape. The flock 720 and 726 extend from the distal ends a predetermined longitudinal distance. The predetermined longitudinal distance is at least as long as the depth of a post hole. A three dimensional marking 731 may be placed on the second handle portion to distinguish the first brush or flock 720 from the second brush or flock 726. The first and second handle portions 712 and 714 as well has the first and second reduced diameter portions 721 and 727 may be molded as a single piece of plastic. The first and second brush or flock 720 and 726 is then placed or formed on the first and second reduced diameter portions 721 and 727 with adhesive or by any other suitable technique.

Figure 12:
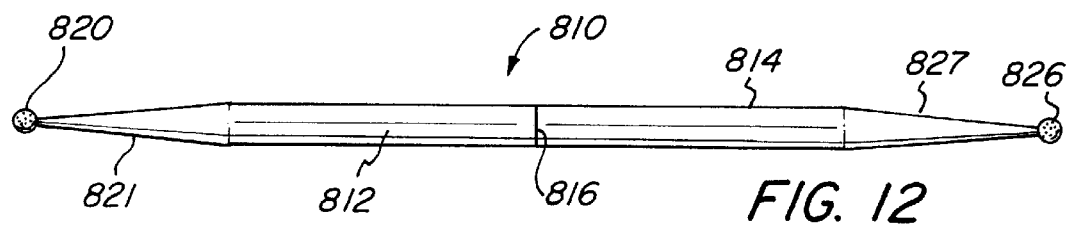
FIG. 12 is a side elevational view of another embodiment of the present invention.

FIG. 12 illustrates another embodiment of the present invention. In this embodiment applicator 810 has a bendable first reduced diameter portion 821 and a bendable second reduced diameter portion 827. The bendable first and second reduced diameter portions are examples of a molded flexible shape that is bendable. The first handle portion 812 and the second handle portion 814 together with the reduced diameter portion 821 and the second reduced diameter portions 827 may be molded as a single piece of plastic. Adjacent the distal end of the first reduced diameter portion 821 is a first foam ball 820. Adjacent the distal end of the second reduced diameter portion 827 is a second foam ball 826. The first and second reduced diameter portions 821 and 827 are conical in shape. This helps to improve visibility when working in relatively small areas. A score or scribe line 816 is placed between the first and second handle portions permitting the easy separation of the first and second handle portions 812 and 814, thereby forming two independent applicators if desired.

Figure 13:
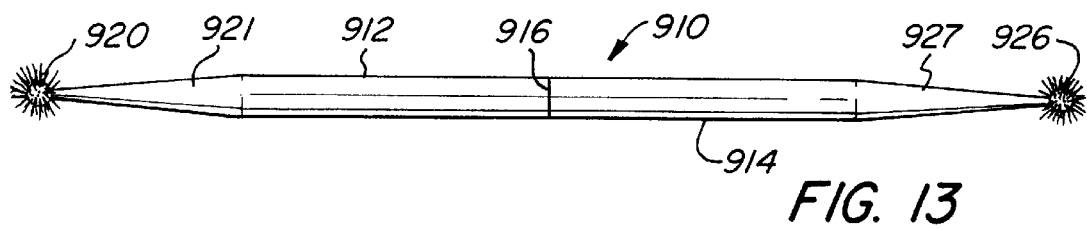
FIG. 13 is a side elevational view of another embodiment of the present invention.

FIG. 13 illustrates an embodiment of the invention similar to the embodiment illustrated in FIG. 12, however with a different applicator material. In this embodiment the applicator 910 has a first handle portion 912 and a second handle portion 914 separated by a frangible score or scribe line 916. Formed as part of the first handle portion 912 is a first reduced diameter portion 921. On the distal end of the first reduced diameter portion 921 is a fuzzy ball or flock ball 920. Formed as part of the second handle portion 914 is a second reduced diameter portion 927. On the distal end of the second reduced diameter portion 927 is a fuzzy ball or flock ball 926.

Figure 14:
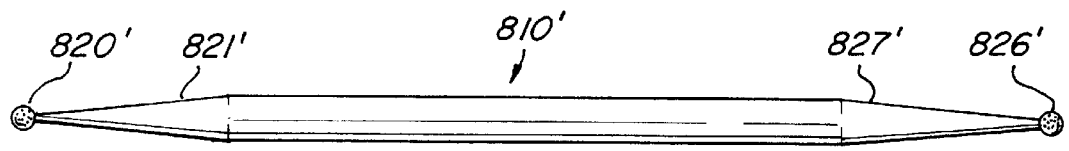
FIG. 14 is a side elevational view of another embodiment of the present invention similar to that of FIG. 12 but without a score or scribe line.

FIG. 14 illustrates another embodiment of the present invention similar to FIG. 12, however without a score or scribe line. In this embodiment applicator 810' has a first reduced diameter or tapered portion 821' and a second reduced diameter or tapered portion 827'. Placed at the end of each first and second portions 821' and 827' are first and second foam balls 820' and 826'.

Figure 15:
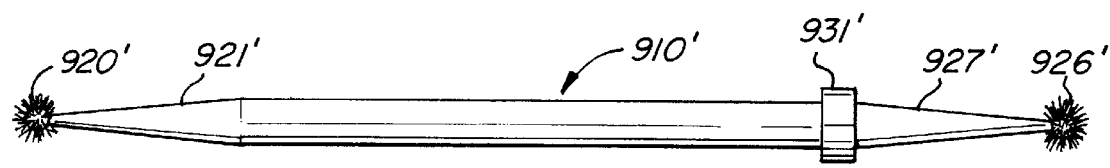
FIG. 15 is a side elevational view of another embodiment of the present invention similar to that of FIG. 13 but without a score or scribe line and having a means for identifying one end.

FIG. 15 illustrates another embodiment of the present invention similar to FIG. 13, however without a score or scribe line and with a means for identifying one end. In this embodiment applicator 910' has a first reduced diameter or tapered portion 921' and a second reduced diameter or tapered portion 927'. Placed at the end of each first and second portions 921' and 927' are first and second fuzzy or flock balls 920' and 926'. A crimp or marking 931' is placed adjacent one end of the applicator 910' The crimp or marking 931' is a means for identifying one end of the applicator 910'. The crimp or marking 931' helps to identify the different ends of the applicator 910' so that two different materials can be applied without mixing or contamination. While FIGS. 14 and 15 illustrate an embodiment without a scribe or score line, it should be understood that any of the embodiments illustrated in the other figures could also be made without a scribe or score line in practicing the present invention. For example, a double ended brush applicator could be used without a score or scribe line. The brush applicator could be used to save time in a procedure were two different liquids must be used. The double ended brush applicator, by permitting the dentist to quickly rotate the double ended brush applicator, greatly reduces the time needed to apply liquid materials. Accordingly, the dentist can alternately apply two different materials to a single patient quickly and easily with minimum waste of time and materials, greatly reducing cost to the patient.

Accordingly, it should be appreciated that the present invention, in providing a relatively inexpensive, disposable applicator handle having an integrally formed applicator on either end greatly reduces cost and waste. Additionally, the present invention, by providing a scribe or score line intermediate either end provides the user with flexibility in using either a double ended applicator or two independent and separate single ended applicators. While a scribe line or score line has been illustrated, it should be appreciated that any structure that permits the applicator handle to be separated into a first and second portion would be equivalent. A bendable portion having a crimp, hinge, or shape has been illustrated. However, a suitable plastic material may be selected that will permit bending without a crimp or hinge. Additionally, while the handle portion has been illustrated as being tubular, the handle may be made of a solid material or of any shape.

While the present invention has been illustrated and described with respect to several embodiments, it should be appreciated that various modifications may be made without departing from the spirit and scope of this invention.

What is claimed is:

1. A method of coating the internal surfaces of a post hole located in a tooth comprising the steps of:

forming a post hole in a tooth to a predetermined depth, placing a fluent dental material intended to line the interior surfaces of a post hole onto an applicator having an applicating end defined as an elongated spiral having minute radially extending flocking disposed along the longitudinal length of said spiral, said applicating end so formed being of a size to be received in said post hole formed in a tooth, rotating said dental applicator so formed so that the radially extending fibers are rotated whereby the spiral causes the fluent dental material on the applicating end to be placed onto the interior surface of the post hole in an up and down movement as the applicator is rotated to ensure a uniform coating of the internal surfaces of a post hole, and removing the dental applicator from the post hole upon the coating of the internal surfaces of said post hole.

* * * * *